US011560069B2

(12) United States Patent
Kim

(10) Patent No.: US 11,560,069 B2
(45) Date of Patent: Jan. 24, 2023

(54) MEASUREMENT DEVICE FOR VEHICLE SEAT

(71) Applicant: NHK SPRING CO., LTD., Yokohama (JP)

(72) Inventor: Donghyoun Kim, Yokohama (JP)

(73) Assignee: NHK SPRING CO., LTD, Kanagawa (JP)

( * ) Notice: Subject to any disclaimer, the term of this patent is extended or adjusted under 35 U.S.C. 154(b) by 259 days.

(21) Appl. No.: 17/082,110

(22) Filed: Oct. 28, 2020

(65) Prior Publication Data

US 2021/0129708 A1     May 6, 2021

(30) Foreign Application Priority Data

Nov. 1, 2019    (JP) .............................. JP2019-200216

(51) Int. Cl.
| | | |
|---|---|---|
| *B60N 2/879* | (2018.01) | |
| *B60N 2/00* | (2006.01) | |
| *A61B 5/00* | (2006.01) | |
| *G01L 5/00* | (2006.01) | |
| *A61B 5/282* | (2021.01) | |
| *A61B 5/352* | (2021.01) | |

(52) U.S. Cl.
CPC .............. *B60N 2/002* (2013.01); *A61B 5/282* (2021.01); *A61B 5/352* (2021.01); *A61B 5/6893* (2013.01); *B60N 2/879* (2018.02); *G01L 5/00* (2013.01)

(58) Field of Classification Search
CPC ........ B60N 2/002; B60N 2/879; A61B 5/282; A61B 5/352; A61B 5/6893; G01L 5/00
See application file for complete search history.

(56) References Cited

U.S. PATENT DOCUMENTS

| | | | | |
|---|---|---|---|---|
| 7,629,546 B2 * | 12/2009 | Saitoh | ................ | G01G 19/4142 200/85 A |
| 7,642,985 B2 * | 1/2010 | Ito | ........................ | B60N 2/0276 340/562 |
| 7,967,377 B2 * | 6/2011 | Truckenbrodt | ........ | B60N 2/829 297/410 |
| 9,693,726 B2 * | 7/2017 | Sugiyama | ............. | B60W 40/08 |
| 10,143,841 B2 * | 12/2018 | Medford | ................ | B60N 2/879 |
| 10,244,959 B2 * | 4/2019 | Sugiyama | ............. | B60N 2/002 |
| 10,434,965 B2 * | 10/2019 | Han | ........................ | B60N 2/26 |

(Continued)

FOREIGN PATENT DOCUMENTS

JP          2016-185778       10/2016

*Primary Examiner* — Philip F Gabler
(74) *Attorney, Agent, or Firm* — Dority & Manning, P.A.

(57) ABSTRACT

A measurement device for a vehicle seat includes a memory; a processor coupled to the memory; a headrest body of a headrest; a first side section of the headrest that is swingable toward a seat front side so as to support the neck of the vehicle occupant; a second side section of the headrest that is swingable toward the seat front side so as to support the neck of the vehicle occupant; a first electrode provided at the first side section and contacting the neck in a state in which the first side section is supporting the neck; and a second electrode provided at the second side section and contacting the neck in a state in which the second side section is supporting the neck. The processor is configured to acquire a waveform of a potential difference based on the potential difference between the first electrode and the second electrode over time.

5 Claims, 5 Drawing Sheets

(56) References Cited

U.S. PATENT DOCUMENTS

| | | | | |
|---|---|---|---|---|
| 10,458,787 B2* | 10/2019 | Kwon | ................ | B60Q 9/00 |
| 2010/0148559 A1* | 6/2010 | Prokop | ................ | B60R 25/24 |
| | | | | 297/391 |
| 2014/0350411 A1* | 11/2014 | Gussen | ................ | B60N 2/879 |
| | | | | 607/107 |
| 2018/0118071 A1* | 5/2018 | Sugiyama | ................ | A47C 7/14 |
| 2019/0038231 A1* | 2/2019 | Sugiyama | ................ | A61B 5/18 |
| 2021/0402891 A1* | 12/2021 | Oommen | ................ | B60N 2/64 |

* cited by examiner

MEASUREMENT DEVICE FOR VEHICLE SEAT

CROSS-REFERENCE TO RELATED APPLICATION

This application claims priority under 35 USC 119 from Japanese Patent Application No. 2019-200216 filed Nov. 1, 2019, the disclosure of which is incorporated by reference herein in its entirety.

BACKGROUND

Technical Field

The present disclosure relates to a measurement device for a vehicle seat.

Related Art

Japanese Patent Application Laid-Open (JP-A) No. 2016-185778 discloses an invention relating to a vehicle seat. The vehicle seat is equipped with a heart rate sensor capable of measuring the heart rate of an occupant based on a biosignal from the occupant.

SUMMARY

However, in the related art disclosed in JP-A No. 2016-185778, the heart rate sensor is configured by an electrostatic capacitive sensor. If the relative positional relationships between the electrodes of the heart rate sensor and the occupant change, for example if the occupant moves around on the vehicle seat, a biosignal waveform obtained by the heart rate sensor may change.

Namely, the related art leaves room for improvement on the perspective of the accuracy of a waveform of a biosignal detected from the occupant.

In consideration of the above circumstances, the present disclosure obtains a measurement device for a vehicle seat capable of improving the accuracy of a waveform of a biosignal detected from a vehicle occupant.

A measurement device for a vehicle seat of a first aspect of the present disclosure includes a memory, a processor coupled to the memory, a headrest body of a headrest that is attachable to a seatback, and the headrest body is configured to support a head of a vehicle occupant from a seat rear side, a first side section of the headrest that is attached to one side in a seat width direction of the headrest body so as to be capable of swinging toward a seat front side, and that is configured to support a neck of the vehicle occupant in a state in which the first side section has been swung toward the seat front side, a second side section of the headrest that is attached to another side in the seat width direction of the headrest body so as to be capable of swinging toward the seat front side, and that is configured to support the neck of the vehicle occupant in a state in which the second side section has been swung toward the seat front side, a first electrode that is provided at the first side section, and that is configured to contact the neck of the vehicle occupant in a state in which the first side section is supporting the neck, and a second electrode that is provided at the second side section, and that is configured to contact the neck of the vehicle occupant in a state in which the second side section is supporting the neck. The processor is configured to acquire a waveform of a potential difference based on the potential difference between the first electrode and the second electrode over time.

According to the measurement device for a vehicle seat of the first aspect, the back of the vehicle occupant is supported by the seatback, and the head of the vehicle occupant is supported from the seat rear side by the headrest attached to the seatback.

The headrest body configures a main section of the headrest. The first side section that configures part of the headrest is attached to the one side in the seat width direction of the headrest body, and the second side section that also configures part of the headrest is attached to the other side in the seat width direction of the headrest body.

The first electrode is provided at the first side section, and the second electrode is provided at the second side section. The processor acquires a waveform of the potential difference based on the potential difference between the first electrode and the second electrode over time. Thus, in the present aspect, as long as the first electrode and the second electrode are in a state capable of acquiring a bio-potential from the vehicle occupant, a waveform of a biosignal can be acquired from the vehicle occupant.

In order for the first electrode and the second electrode to acquire the bio-potential from the vehicle occupant stably, the first electrode and the second electrode preferably contact the vehicle occupant in a state in which the relative positional relationships between the vehicle occupant and the first electrode and the second electrode remain constant.

In the present aspect, the first side section is swung toward the seat front side with respect to the headrest body such that the neck of the vehicle occupant is supported by the first side section. The first electrode contacts the neck in a state in which the first side section is supporting the neck. Moreover, the second side section is swung toward the seat front side with respect to the headrest body such that the neck of the vehicle occupant is supported by the second side section. The second electrode contacts the neck in a state in which the second side section is supporting the neck.

This enables the first electrode and the second electrode to contact the vehicle occupant in a stable state, allowing the first electrode and the second electrode to acquire the bio-potential from the vehicle occupant stably.

A measurement device for a vehicle seat of a second aspect of the present disclosure is the first aspect, wherein the processor is configures to extract plural waveforms with different frequencies from the waveform of the potential difference.

According to the measurement device for a vehicle seat of the second aspect, the processor is configured to extract plural waveforms with different frequencies from the waveform of the potential difference between the first electrode and the second electrode. This enables waveforms of various bio-signals relating to states of the vehicle occupant to be acquired.

A measurement device for a vehicle seat of a third aspect of the present disclosure is the first aspect or the second aspect, wherein the processor is configured to acquire an electrocardiogram waveform of the vehicle occupant from the waveform of the potential difference, and measuring an interval between R waves on the electrocardiogram waveform.

According to the measurement device for a vehicle seat of the third aspect, the processor is configured to acquire an electrocardiogram waveform of the vehicle occupant, and measure the interval between the R waves on the electrocardiogram waveform. This enables fluctuations in the heart rate of the vehicle occupant to be observed.

A measurement device for a vehicle seat of a fourth aspect of the present disclosure is any one of the first aspect to the third aspect, further includes a seated state detection section configured to output a detection signal when sitting of the vehicle occupant has been detected, a first actuator configured to swing the first side section toward the seat front side, a second actuator configured to swing the second side section toward the seat front side, a first pressure detection section that is provided at the first side section and that is configured to output a first pressure signal when pressure received from the neck has reached a predetermined value, and a second pressure detection section that is provided at the second side section and that is configured to output a second pressure signal when pressure received from the neck has reached a predetermined value. Moreover, the processor is configured to drive the first actuator so as to swing the first side section toward the seat front side based on the detection signal, drive the second actuator so as to swing the second side section toward the seat front side based on the detection signal, and stop the first actuator and the second actuator based on the first pressure signal and the second pressure signal.

According to the measurement device for a vehicle seat of the fourth aspect, the seated state detection section outputs a detection signal when the vehicle occupant sits on the vehicle seat. Based on the detection signal from the seated state detection section, the processor swings the first side section and the second side section toward the seat front side using the first actuator and the second actuator respectively.

However, if the first side section and the second side section were to be swung too far toward the seat front side, the first side section and the second side section might constrict the neck of the vehicle occupant excessively.

The present aspect includes the first pressure detection section provided at the first side section and the second pressure detection section provided at the second side section. When the pressure received from the neck of the vehicle occupant by the first pressure detection section reaches the predetermined value, the first pressure detection section outputs the first pressure signal. Similarly, when the pressure received from the neck of the vehicle occupant by the second pressure detection section reaches the predetermined value, the second pressure detection section outputs the second pressure signal.

The processor stops the first actuator and the second actuator based on the first pressure signal and the second pressure signal, thereby stopping the swinging of the first side section and the second side section. The first side section and the second side section are thus prevented from constricting the neck of the vehicle occupant excessively, thereby suppressing any effect on the bio-potential of the vehicle occupant.

A measurement device for a vehicle seat of a fifth aspect of the present disclosure is the fourth aspect, further includes a release device that is operable by the vehicle occupant. The processor is configured to drive the first actuator and the second actuator so as to return the first side section and the second side section to an initial state, as a result of operation of the release device by the vehicle occupant.

According to the measurement device for the vehicle seat of the fifth aspect, when the vehicle occupant operates the release device, the processor drives the first actuator and the second actuator so as to return the first side section and the second side section to their initial states. The vehicle occupant is thus able to stop bio-signal detection when the vehicle occupant has deemed that bio-signal detection is not appropriate, such as when the vehicle occupant is wearing clothing or the like that covers the neck.

As described above, the measurement device for a vehicle seat according to the present disclosure exhibits the excellent advantageous effect of enabling the accuracy on a waveform of a bio-signal detected from the vehicle occupant to be improved.

BRIEF DESCRIPTION OF THE DRAWINGS

Preferred embodiments will be described in detail based on the following figures, wherein.

DETAILED DESCRIPTION

Figure 1:
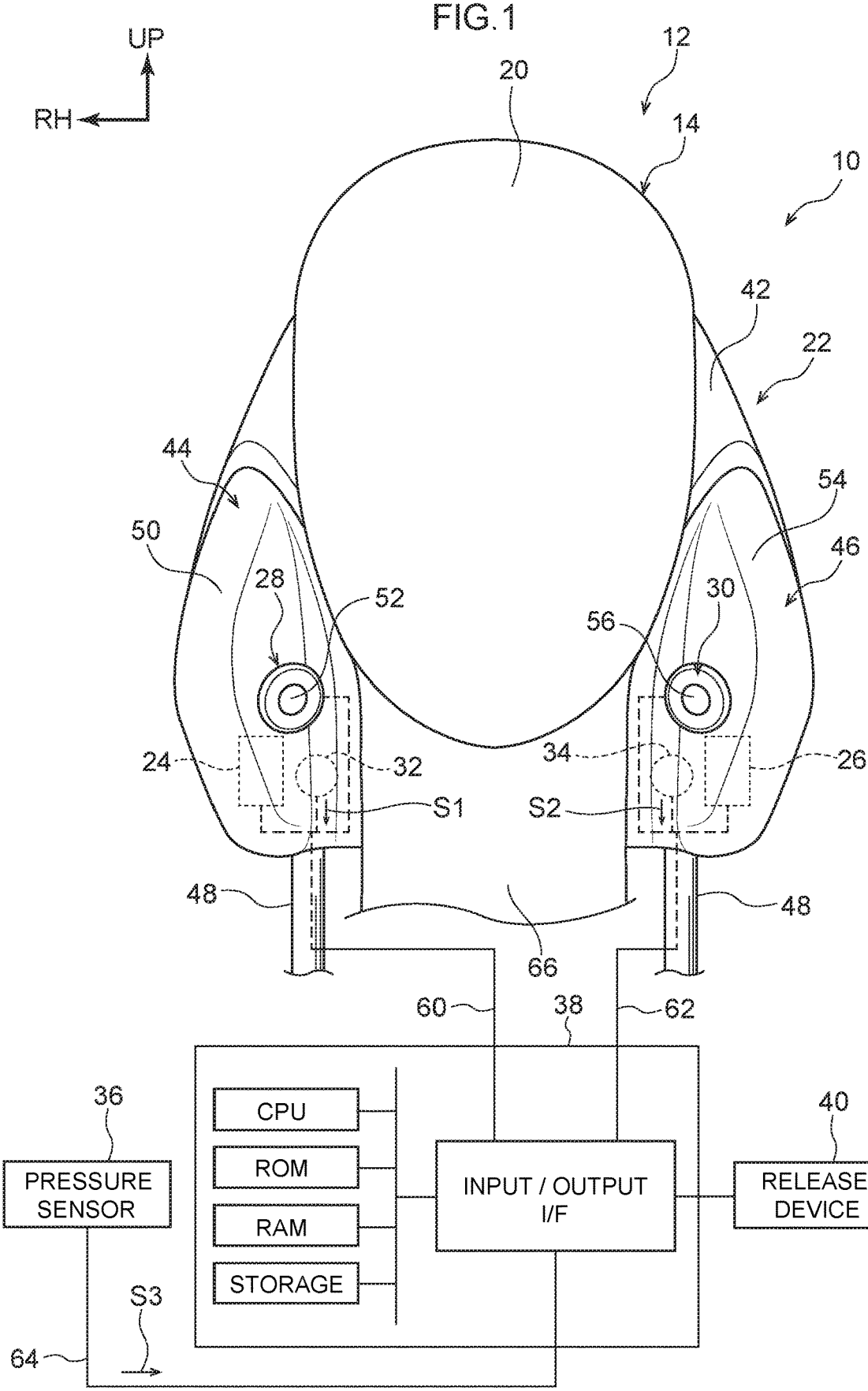
FIG. 1 is a front view schematically illustrating a state in which a measurement device for a vehicle seat according to an exemplary embodiment is not in operation.

Explanation follows regarding an example of an exemplary embodiment of a measurement device for a vehicle seat according to the present disclosure, with reference to FIG. 1 to FIG. 5B. Note that in the drawings, the arrow FR, the arrow UP, and the arrow RH respectively indicate a forward direction, an upward direction, and a rightward direction of a vehicle seat 12 (hereafter referred to as the seat 12) equipped with parts of a measurement device for a vehicle seat 10 (hereafter referred to as the measurement device 10) according to the present exemplary embodiment, as appropriate.

Figure 2:
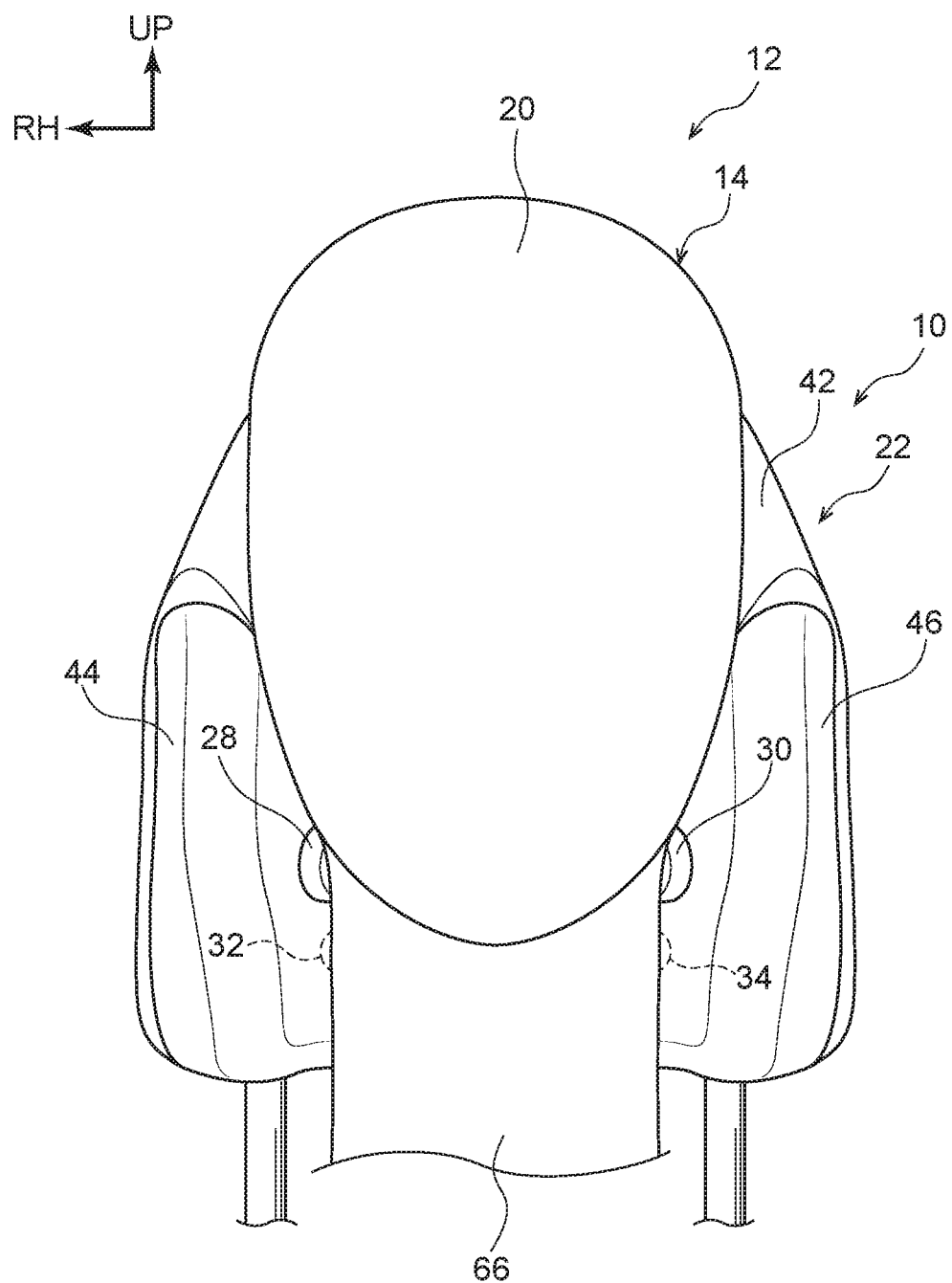
FIG. 2 is a front view schematically illustrating a state in which a measurement device for a vehicle seat according to an exemplary embodiment is in operation.
Figure 3:
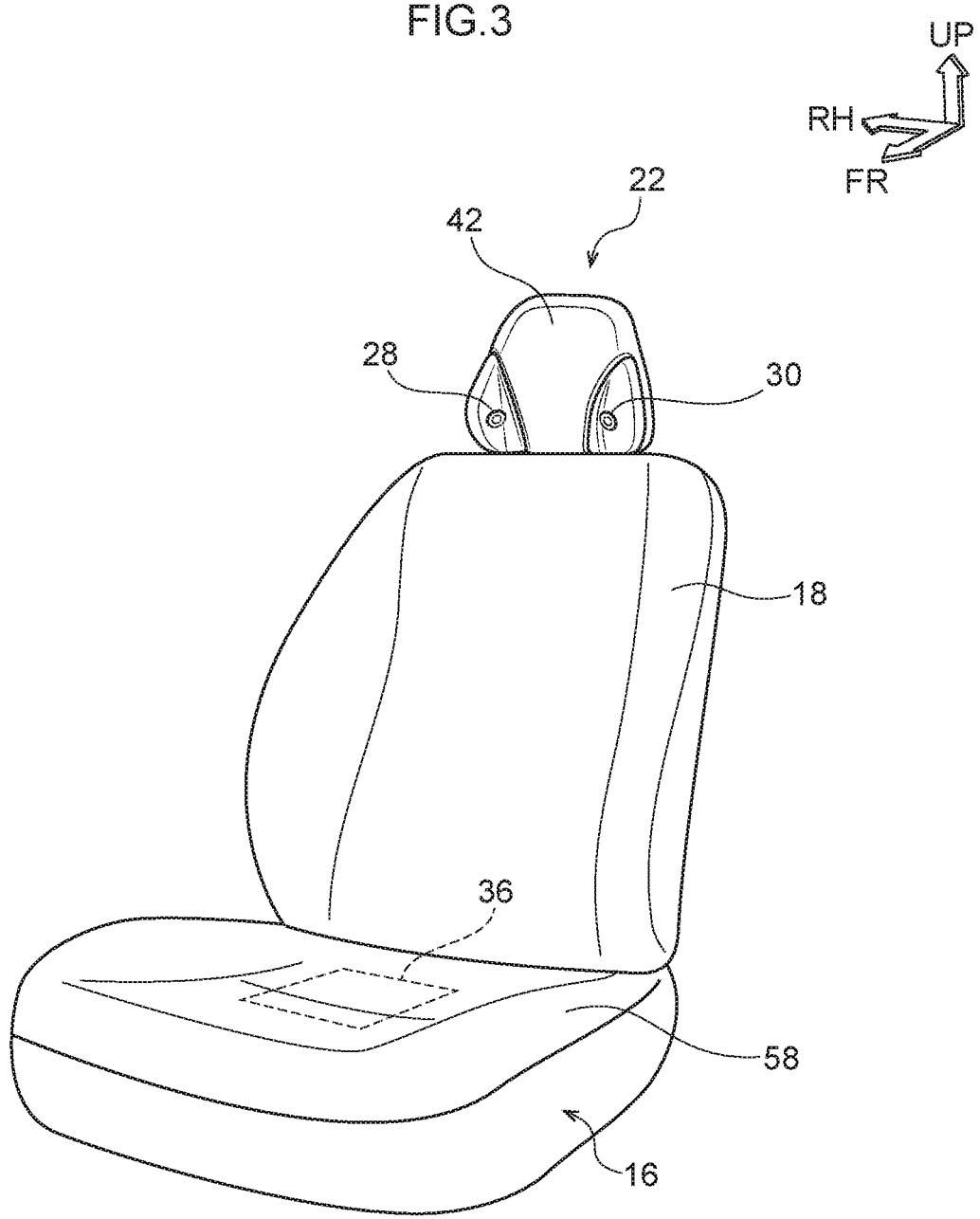
FIG. 3 is a perspective view schematically illustrating a configuration of a vehicle seat equipped with a measurement device according to an exemplary embodiment.

First, explanation follows regarding configuration of the seat 12, with reference to FIG. 1 to FIG. 3. The seat 12 includes a seat cushion 16 that supports the buttocks and thighs of an occupant 14, a seatback 18 that supports the back of the occupant 14, and a headrest 22 that supports the head 20 of the occupant 14.

The measurement device 10 is configured including the headrest 22, an actuator 24 serving as a first actuator, an actuator 26 serving as a second actuator, an electrode 28 serving as a first electrode, an electrode 30 serving as a second electrode, a pressure sensor 32 serving as a first pressure detection section, a pressure sensor 34 serving as a second pressure detection section, a pressure sensor 36 serving as a seated state detection section, a control section 38, and a release device 40.

The headrest 22 includes a headrest body 42 configuring a main section thereof, a side section 44 serving as a first side section, and a side section 46 serving as a second side section. The headrest 22 is formed in a trapezoidal shape that widens on progression from a seat upper side toward a seat lower side as viewed along a seat front-rear direction.

The headrest body 42 is provided with a pair of headrest stays 48 that extend from the headrest body 42 toward the seat lower side. The respective headrest stays 48 are supported by non-illustrated holder portions provided at the seatback 18, such that positions in the seat up-down direction of the headrest stays 48 relative to the holder portions are adjustable within a predetermined range. The position in the seat up-down direction of the headrest 22 relative to the seatback 18 is therefore adjustable.

The side section 44 is attached to a right side in a seat width direction and at a seat lower side section of the headrest body 42 such that the side section 44 is capable of swinging about the seat up-down direction centered on a central section in the seat width direction of the side section 44.

The side section 46 is attached to a left side in the seat width direction at a seat lower side section of the headrest body 42 such that the side section 46 is also capable of swinging about the seat up-down direction centered on a central section in the seat width direction of the side section 46.

The actuator 24 is built into a non-illustrated pad portion of the side section 44, and is configured including a non-illustrated motor and worm gear. A worm of the worm gear is provided at a shaft of the motor. A worm wheel of the worm gear is provided at a non-illustrated shaft that axially supports the side section 44 with respect to the headrest body 42. When the motor of the actuator 24 is driven, the side section 44 swings about the seat up-down direction.

The actuator 26 is built into a non-illustrated pad portion of the side section 46. The actuator 26 is configured similarly to the actuator 24, with the exception that the worm wheel of the actuator 26 is provided on a non-illustrated shaft that axially supports the side section 46 with respect to the headrest body 42. When the motor of the actuator 26 is driven, the side section 46 swings about the seat up-down direction.

The electrodes 28, 30 are both used to detect voltage. A main portion of the electrode 28 is embedded in the non-illustrated pad portion of the side section 44, in a state in which a contact face 52 of the electrode 28 is exposed through a cover 50 of the side section 44 so as to be capable of contacting a measurement subject.

Similarly, a main portion of the electrode 30 is embedded in the non-illustrated pad portion of the side section 46, in a state in which a contact face 56 of the electrode 30 is exposed through a cover 54 of the side section 46 so as to be capable of contacting the measurement subject.

The pressure sensor 32 is disposed between the non-illustrated pad portion of the side section 44 and the cover 50. The pressure sensor 32 is capable of outputting a signal S1 serving as a first pressure signal when pressure applied to the pressure sensor 32 reaches a predetermined value.

Similarly, the pressure sensor 34 is disposed between the non-illustrated pad portion of the side section 46 and the cover 54. The pressure sensor 34 is capable of outputting a signal S2 serving as a second pressure signal when pressure applied to the pressure sensor 34 reaches a predetermined value.

The pressure sensor 36 is disposed between a non-illustrated pad portion of the seat cushion 16 and a cover 58. The pressure sensor 36 is capable of outputting a signal S3 serving as a detection signal when pressure applied to the pressure sensor 36 reaches a predetermined value.

The control section 38 is disposed at a seat lower side of the seat 12. The control section 38 is electrically connected to the actuators 24, 26, the electrodes 28, 30, and the pressure sensors 32, 34 through leads 60, 62 that are internally routed through the headrest stays 48. The control section 38 is also electrically connected to the pressure sensor 36 through a lead 64. Note that the control section 38 is supplied with power from a non-illustrated onboard power source.

Specifically, the control section 38 is configured including a central processing unit (CPU), read only memory (ROM), random access memory (RAM), storage (a storage section), and an input/output I/F.

The CPU serves as a central processing unit (computation section) that is capable of executing various programs. The CPU is capable of reading programs from the ROM and executing various programs using the RAM as a workspace.

In the present exemplary embodiment, the CPU reads and executes an execution program stored in the ROM to enable the control section 38 to exhibit various functions, as described below.

Specifically, the actuators 24, 26 and the pressure sensors 32, 34, 36 are connected to the input/output I/F. When the occupant 14 is seated, the control section 38 controls operation of the actuators 24, 26 based on signals from the pressure sensors 32, 34, 36.

Specifically, when the signal S3 is input from the pressure sensor 36 as a result of the occupant 14 sitting on the seat 12, the control section 38 drives the actuators 24, 26 so as to swing the side sections 44, 46 toward the seat front side as illustrated in FIG. 2. The side sections 44, 46 swing until they abut the neck 66 of the occupant 14, such that the neck 66 is supported by the side sections 44, 46. The electrodes 28, 30 are thereby placed in a state of contact with the neck 66 of the occupant 14. Note that the height of the headrest 22 is adjusted such that the electrodes 28, 30 contact the neck 66 of the occupant 14 in the vicinity of the semispinalis capitis.

The control section 38 is configured to stop the actuators 24, 26 when the signal S1 from the pressure sensor 32 and the signal S2 from the pressure sensor 34 are respectively input as a result of the neck 66 of the occupant 14 being pressed by the side sections 44, 46.

The input/output I/F is connected to the electrodes 28, 30 in order to store the potential difference between the electrode 28 and the electrode 30 in the storage at predetermined intervals. The control section 38 is then capable of acquiring a potential difference waveform based on the potential difference between the electrode 28 and the electrode 30 over time. Namely, a waveform of the potential differences between the electrode 28 and the electrode 30 at the neck 66 of the occupant 14, more specifically, an electromyogram of the semispinalis capitis of the occupant 14, is acquired.

The control section 38 includes a non-illustrated low pass filter or the like, enabling plural waveforms of different frequencies to be extracted from the waveform of the potential difference between the electrode 28 and the electrode 30.

For example, the control section 38 is capable of acquiring an electrocardiogram waveform for the occupant 14 from the acquired semispinalis capitis electromyogram of the occupant 14, and is capable of measuring the interval between R waves (RRI) in this electrocardiogram waveform. Namely, the control section 38 also functions as a measurement section.

The release device 40 includes a non-illustrated push switch provided at the seat 12, and is electrically connected to the control section 38. When the occupant 14 operates the push switch, the control section 38 drives the actuators 24, 26 so as to swing the side sections 44, 46 toward the seat rear side and thereby return the side sections 44, 46 to their initial states.

Operation and Advantageous Effects of Present Exemplary Embodiment

Next, explanation follows regarding operation and advantageous effects of the present exemplary embodiment.

As illustrated in FIG. 3, the back of the occupant 14 is supported by the seatback 18, and the head 20 of the occupant 14 is supported from the seat rear side by the headrest 22 attached to the seatback 18.

The main section of the headrest 22 is configured by the headrest body 42. The side section 44 that configures part of the headrest 22 is attached to the one lateral side of the headrest body 42, and the side section 46 that also configures part of the headrest 22 is attached to the other lateral side of the headrest body 42.

Figure 4:
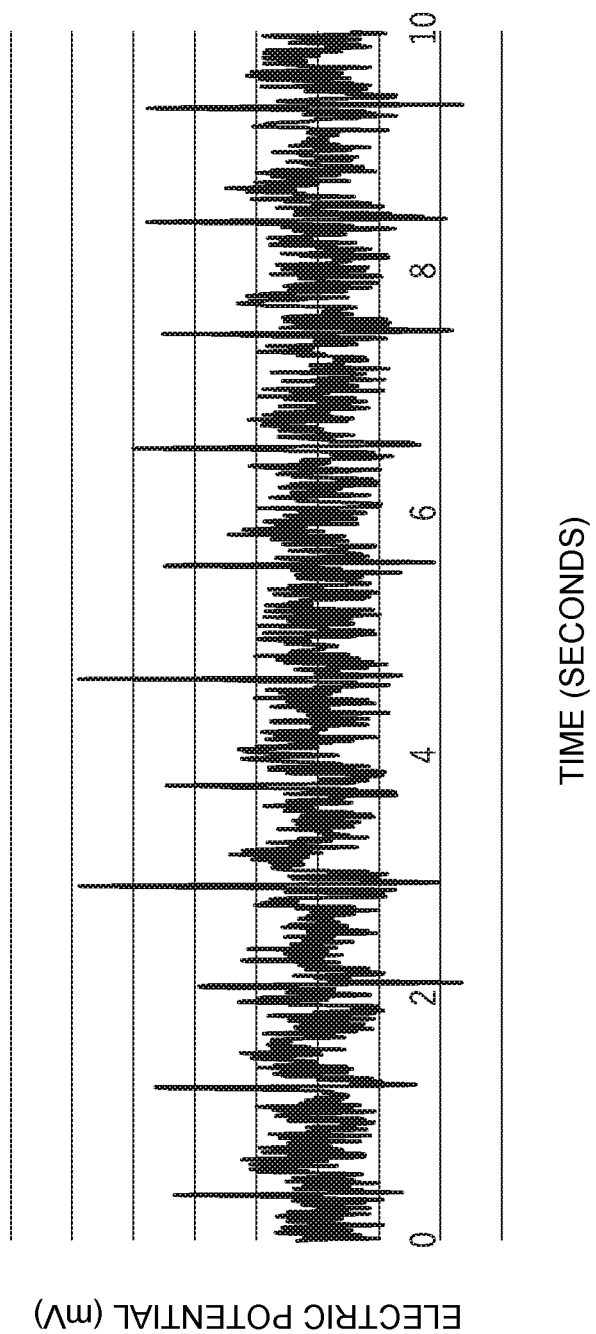
FIG. 4 is a graph illustrating bio-signal data from an occupant in time-series.

The electrode 28 is provided at the side section 44, and the electrode 30 is provided at the side section 46. As illustrated in FIG. 4, the control section 38 acquires a waveform of a potential difference based on the potential difference between the electrode 28 and the electrode 30 over time. Thus, as long as the electrode 28 and the electrode 30 are in a state capable of acquiring a bio-potential from the occupant 14, a biosignal waveform can be acquired from the occupant 14.

In order for the electrode 28 and the electrode 30 to acquire the bio-potential from the occupant 14 stably, the electrode 28 and the electrode 30 preferably contact the occupant 14 in a state in which the relative positional relationships between the occupant 14 and the electrode 28 and electrode 30 remain constant.

The side section 44 is swung toward the seat front side with respect to the headrest body 42 such that the neck 66 of the occupant 14 is supported by the side section 44. The electrode 28 contacts the neck 66 in a state in which the side section 44 is supporting the neck 66. Moreover, the side section 46 is swung toward the seat front side with respect to the headrest body 42 such that the neck 66 of the occupant 14 is supported by the side section 46. The electrode 30 contacts the neck 66 in a state in which the side section 46 is supporting the neck 66.

This enables the electrode 28 and the electrode 30 to contact the occupant 14 in a stable state, allowing the electrode 28 and the electrode 30 to acquire the bio-potential from the occupant 14 stably.

The control section 38 extracts plural waveforms with different frequencies from the waveform of the potential difference between the electrode 28 and the electrode 30. This enables waveforms of various biosignals relating to states of the occupant 14 to be acquired.

Figure 5A:
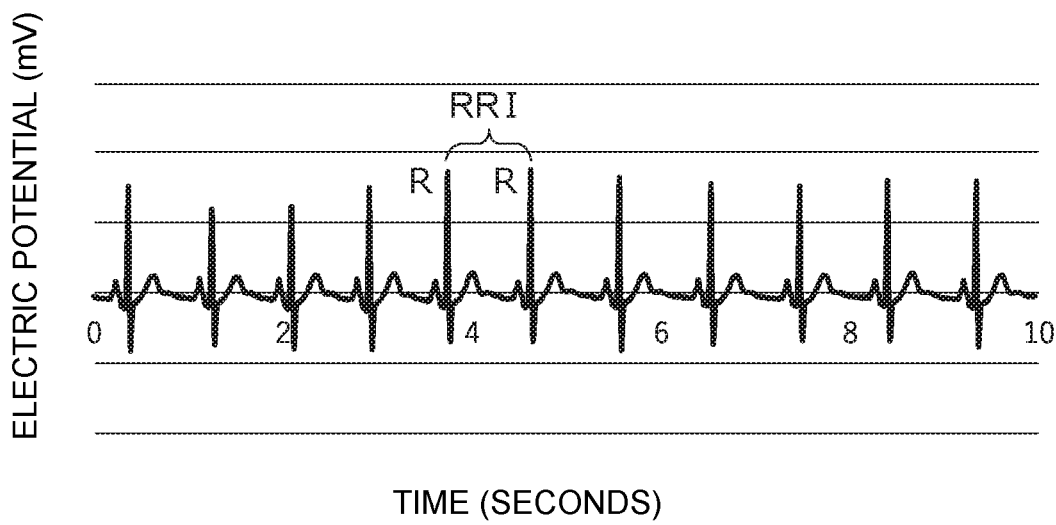
FIG. 5A is an electrocardiogram for an occupant, extracted from a waveform of bio-signals from the occupant.

Specifically, as illustrated in FIG. 5A, in the present exemplary embodiment, an electrocardiogram waveform for the occupant 14 is acquired, and the R wave interval, i.e. the RRI, of this electrocardiogram waveform is measured. This enables fluctuations in the heart rate of the occupant 14 to be observed.

Figure 5B:
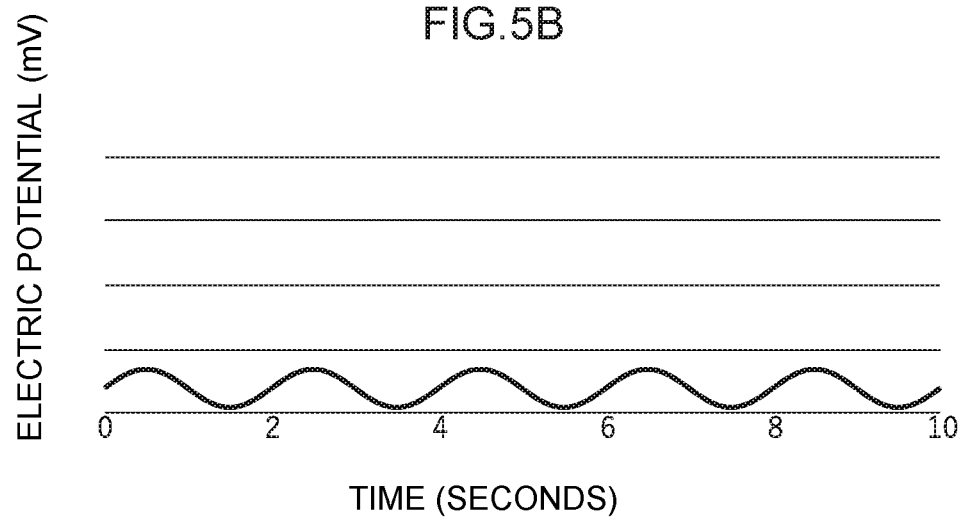
FIG. 5B is an electromyogram for the vicinity of the orbicularis oculi of the occupant, extracted from a waveform of bio-signals from the occupant.

Since behavior of the semispinalis capitis is related to behavior of the orbicularis oculi, a signal relating to the behavior of the orbicularis oculi of the occupant 14 can be extracted from the waveform in FIG. 4, this being an electromyogram of the semispinalis capitis of the occupant 14. As illustrated in FIG. 5B, an electromyogram of the orbicularis oculi of the occupant 14 is thereby acquired.

The signal S3 is output from the pressure sensor 36 when the occupant 14 sits on the seat. Based on the signal S3, the side section 44 and the side section 46 are then swung toward the seat front side by the actuator 24 and the actuator 26 respectively.

However, if the side section 44 and the side section 46 were to be swung too far toward the seat front side, the side section 44 and the side section 46 might constrict the neck 66 of the occupant 14 excessively.

The present exemplary embodiment includes the pressure sensor 32 provided at the side section 44, the pressure sensor 34 provided at the side section 46, and the control section 38. When the pressure received from the neck 66 of the occupant 14 by the pressure sensor 32 reaches a predetermined value, the pressure sensor 32 outputs the signal S1. Similarly, when the pressure received from the neck 66 of the occupant 14 by the pressure sensor 34 reaches a predetermined value, the pressure sensor 34 outputs the signal S2.

The control section 38 stops the actuator 24 and the actuator 26 based on the signal S1 and the signal S2, thereby stopping the swinging of the side section 44 and the side section 46. The side section 44 and the side section 46 are thus prevented from constricting the neck 66 of the occupant 14 excessively, thereby suppressing any effect on the bio-potential of the occupant 14.

When the occupant 14 operates the release device 40, the control section 38 drives the actuator 24 and the actuator 26 so as to return the side section 44 and the side section 46 to their initial states. The occupant 14 is thus able to stop bio-signal detection when the occupant 14 has deemed that bio-signal detection is not appropriate, such as when the occupant 14 is wearing clothing or the like that covers the neck 66.

Thus, the present exemplary embodiment enables the accuracy of the detected bio-signal waveform of the occupant 14 to be improved.

Moreover, an electromyogram of the orbiculans oculi of the occupant 14 when alert and an electromyogram of the orbicularis oculi of the occupant 14 when drowsy may be stored in the control section 38, and the control section 38 may compare these electromyograms against an electromyogram of the occupant 14 when seated in the seat 12, thereby enabling the control section 38 to estimate an alertness state of the occupant 14.

Additional Explanation of Exemplary Embodiment (1) In the exemplary embodiment described above, the control section 38 is disposed at the seat lower side of the seat 12, and the pressure sensor 36 is disposed in the seat cushion 16. However, there is no limitation thereto. For example, depending on the specifications of the seat 12 and so on, the control section 38 and the pressure sensor 36 may be provided at the headrest 22.

(2) In the exemplary embodiment described above, the biosignals acquired from the occupant 14 are processed by the control section 38. However, there is no limitation thereto. For example, a communication section may be provided at the seat 12 in order to transmit the biosignals to a server or the like for processing.

What is claimed is:

1. A measurement device for a vehicle seat comprising:
a memory;
a processor coupled to the memory;
a headrest body of a headrest that is attachable to a seatback, the headrest body being configured to support a head of a vehicle occupant from a seat rear side;
a first side section of the headrest, the first side section being attached to one side in a seat width direction of the headrest body so as to be capable of swinging toward a seat front side, and the first side section being configured to support a neck of the vehicle occupant in a state in which the first side section has been swung toward the seat front side;

a second side section of the headrest, the second side section being attached to another side in the seat width direction of the headrest body so as to be capable of swinging toward the seat front side, and the second side section being configured to support the neck of the vehicle occupant in a state in which the second side section has been swung toward the seat front side;

a first electrode provided at the first side section, the first electrode being configured to contact the neck of the vehicle occupant in a state in which the first side section is supporting the neck; and a second electrode provided at the second side section, the second electrode being configured to contact the neck of the vehicle occupant in a state in which the second side section is supporting the neck, wherein the processor is configured to acquire a waveform of a potential difference based on the potential difference between the first electrode and the second electrode over time.

2. The measurement device for a vehicle seat of claim 1, wherein the processor is configured to extract a plurality of waveforms with different frequencies from the potential difference waveform.

3. The measurement device for a vehicle seat of claim 1, wherein the processor is configured to:

acquire an electrocardiogram waveform of the vehicle occupant from the potential difference waveform; and measure an interval between R waves on the electrocardiogram waveform.

4. The measurement device for a vehicle seat of claim 1, further comprising:

a seated state detection section configured to output a detection signal in a case in which sitting of the vehicle occupant has been detected;

a first actuator configured to swing the first side section toward the seat front side;

a second actuator configured to swing the second side section toward the seat front side;

a first pressure detection section that is provided at the first side section and is configured to output a first pressure signal in a case in which pressure received from the neck has reached a predetermined value; and a second pressure detection section that is provided at the second side section and is configured to output a second pressure signal in a case in which pressure received from the neck has reached a predetermined value, wherein:

the processor is configured to:

drive the first actuator so as to swing the first side section toward the seat front side, based on the detection signal;

drive the second actuator so as to swing the second side section toward the seat front side, based on the detection signal; and stop the first actuator and the second actuator based on the first pressure signal and the second pressure signal.

5. The measurement device for a vehicle seat of claim 4, further comprising:

a release device that is operable by the vehicle occupant, wherein the processor is configured to drive the first actuator and the second actuator so as to return the first side section and the second side section to an initial state, as a result of operation of the release device by the vehicle occupant.

* * * * *